United States Patent [19]

Mork et al.

[11] Patent Number: 4,907,251
[45] Date of Patent: Mar. 6, 1990

[54] PATIENT POSITIONING DEVICE IN MEDICAL PANORAMA X-RAY PHOTOGRAPHING APPARATUS

[75] Inventors: Keisuke Mork, Kyoto; Takao Makino, Shiga; Kazuo Nishikawa, Kyoto; Yoshiaki Iwato; Takahiro Yoshimura, both of Osaka, all of Japan

[73] Assignee: Kabushiki Kaisha Morita Seisakusho, Kyoto, Japan

[21] Appl. No.: 166,554

[22] Filed: Mar. 10, 1988

[51] Int. Cl.⁴ .................................................. A61B 6/14
[52] U.S. Cl. ........................................ 378/39; 378/38; 378/170; 378/205
[58] Field of Search .................. 378/206, 205, 170, 38, 378/39, 40

[56] References Cited
U.S. PATENT DOCUMENTS 4,229,656 10/1980 Iversen et al. ....................... 378/206
4,730,351 3/1988 Heumann ............................ 378/205

Primary Examiner—Carolyn E. Fields
Assistant Examiner—David P. Porta
Attorney, Agent, or Firm—Koda & Androlia

[57] ABSTRACT

A patient positioning device in a medical panorama X-ray photographing apparatus in which after data of the relative position of the subject to the X-ray photographing apparatus supplied from a sensor is compared with data of the relative position of a tomographic zone to the X-ray photographing apparatus thus to produce comparison data which is in turn transmitted to a drive circuit, a tomograph forming assembly and/or the subject is moved from coinciding with each other. The device further includes a comparing arithmetic circuit in which the detected position data of the subject and position data of the tomographic zone are arithmetically compared in order to improve operatability and positioning accuracy. The device furthermore includes a sensor which is adjustable for angular and vertical setting with the use of sensing position changing means in order to improve adaptability to individualities of the subject.

11 Claims, 14 Drawing Sheets

PATIENT POSITIONING DEVICE IN MEDICAL PANORAMA X-RAY PHOTOGRAPHING APPARATUS

BACKGROUND OF THE INVENTION

1. Field of the Invention

The present invention relates to a patient positioning device for use with a medical panorama X-ray photographing apparatus, for coinciding a subject portion of a patient to be examined with a tomographic zone of X-ray tomographing apparatus.

2. Prior Art

It is understood that to take a panoramic X-ray picture of high precision with the use of a medical panorama X-ray photographing apparatus, the coincidence of a portion of the patient to be tomographed (referred to as a subject hereinafter) with the tomographic zone of X-ray tomographing apparatus (referred to as a tomographic zone hereinafter) must be greatly considered. In the prior art, the positioning of the tomographic zone to an appropriate position is made by displacing a patient holding means or tomograph forming assembly automatically or manually with the use of designating means such as gauge, bite-block, light beam, etc. Then, the resulting position is checked by the operator through his visual observation.

However, in such positioning with visual observation by an operator, it will likely cause error resulting from visual error such as parallax. Particularly in the dental field, such positioning is commonly made in relation to a position of the front teeth of patient. In this case, it is very difficult to coincide the front teeth with a tomographic zone because the tomographic zone adapted to the front teeth has a depth of only a few mm. Thus substantially high skill and experience is required for the above coincidence.

Additionally, if the positioning is incomplete, the quality of an X-ray photograph will be lessened, thus resulting, at the worst, in extra irradiation of the patient since rephotographing is needed. Thereby, a simple and effective method of positioning has much been desired to be introduced.

SUMMARY OF THE INVENTION

It is a primary object of the present invention to coincide the subject, without regard to physical features of a patient, with a tomographic zone readily and precisely with the use of a position detecting sensor provided in a medical panorama X-ray photographing apparatus.

It is a second object of the present invention to improve the accuracy and operability in coinciding operation, further with the use of a comparing arithmetic circuit.

It is a third object of the present invention to improve the adaptability to individualities of a patient by additionally providing a means for changing a sensing position of the position detecting sensor.

DETAILED DESCRIPTION OF THE INVENTION

Figure 1:
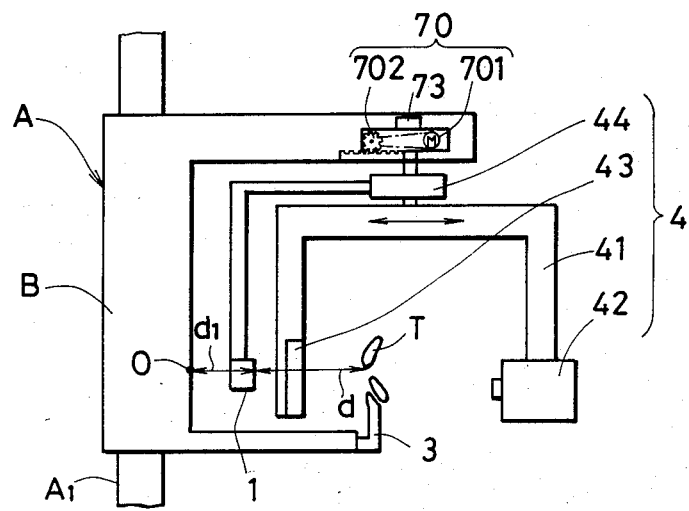
FIG. 1 is a schematic side view of an embodiment of the present invention in the form of a dental X-ray photographing apparatus for the entire jaws.

A patient positioning device in a medical panorama X-ray photographing apparatus, which is arranged to achieve the first object of the present invention, comprises a position detecting sensor 1 for detecting the relative position of the dental arch T of a patient to the X-ray photographing apparatus A, and a drive circuit 5 for moving a tomograph forming assembly 4 and/or a patient holding means 3 in accordance with the comparative data between detected position data from the sensor 1 and relative position data of the tomographic zone P to the X-ray photographing apparatus A.

Another patient positioning device in a medical panorama X-ray photographing apparatus, which is arranged to achieve the second object of the present invention, comprises a position detecting sensor 1 for detecting the relative position of the dental arch T of a patient to the X-ray photographing apparatus A, a comparing arithmetic circuit 2 for comparing detected position data from the sensor 1 with data of the relative position of a tomographic zone P to the X-ray photographing apparatus A, and a drive circuit 5 for moving a tomograph forming assembly 4 and/or a patient holding means 3 in order to coincide the dental arch T with the tomographic zone P upon receiving an output from the comparing arithmetic circuit 2.

A further patient positioning device in a medical panorama X-ray photographing apparatus, which is arranged to achieve the third object of the present invention, comprises a position detecting sensor 1 for detecting the relative position of the dental arch T of a patient to the X-ray photographing apparatus A, a means 8 for changing a sensing position of the sensor 1 and a drive circuit 5 for moving a tomograph forming assembly 4 and/or a patient holding means 3 in accordance with the comparison data between detected position data from the sensor 1 and data of the relative position of a tomographic zone P to the X-ray photographing apparatus A.

Each of the devices according to the present invention is most suitably adapted for use with a dental X-ray photographing apparatus A for the entire jaws which comprises a post A1, a main body B adjustably mounted for vertical movement to the post A1, a tomograph forming assembly 4 suspendedly mounted for horizontally rotating movement to the main body B, and a patient holding means 3 disposed in a rotating circle of the tomograph forming mechanism 4.

The tomograph forming assembly 4 comprises a horizontally rotatable arm 41, an X-ray projector 42 and X-ray film cassette 43 mounted in confronting relationship to each other on both ends of the arm 41 respectively, and a rotating drive mechanism 44 for moving the arm 41 in an appropriate configuration along the dental arch T of a patient, so that the X-ray projector 42 and X-ray film cassette can move in an approximately elliptical circle along the dental arch T of the patient located on the patient holding means 3 in order to record a panoramic tomograph of the dental arch on a film. The rotating drive mechanism 44 is so arranged as to cause the horizontally rotating arm 41 to follow an approximately elliptical track in rotating motion, thus employing various well known mechanisms.

The aforesaid position detecting sensor 1 detects a position of the head of patient located on the patient holding means 3 and outputs data of the relative position of the dental arch T to a reference point 0 defined in the dental X-ray photographing apparatus A. The sensor 1 is situated regardless of the rotating movements of the main body B and tomograph forming assembly 4 in the dental X-ray photographing apparatus A and disposed outside the rotating circle of the tomograph forming assembly 4 and also in an appropriate position on the center line extending across the patient. The sensor 1 is an optical measuring sensor for measuring a distance by detecting a reflected beam of visible light, laser, or infrared rays incident on the teeth (incisor or canine teeth), lip, or cheek of a patient, an ultrasonic type distance measuring sensor, or an optical phase detecting sensor, as the case may be. It is most appropriate that the reference point 0 is a point on the main body B across which the center line of patient extends as it can be established in any place on a fixed portion of the X-ray photographing apparatus A.

The tomographic zone P is a zone in which an X-ray tomographic picture is taken along the dental arch T by the tomograph forming assembly 4. The tomographic zone P may be securely defined to a place in the X-ray photographing apparatus A and additionally, determined by comparing detection data from the sensor 1 with selected output data from the comparing arithmetic circuit 2 which has previously been supplied with the information about typical models of physical features processed from statistically collected data on a multiplicity of patients. More specifically, in the case of the former, the difference data between the detected position data from the sensor 1 and the position data of the tomographic zone P is directly supplied to the drive circuit 5, whereby the tomograph forming assembly 4 and/or patient holding means 8 can be moved to appropriate positions. In the case of the latter, the operator is permitted to select one from the aforesaid models (with the use of a keyboard of a microprocessor 22 as will be depicted later) upon observing the physical features of patient so that the positioning of the patient can be made through the arithmetic operation of comparing the selected tomographic zone P and detection data from the sensor 1 with each other.

Upon receiving a command from the sensor 1 or comparing arithmetic circuit 2, the drive circuit 5 sends a signal for moving the tomograph forming assembly 4 and/or patient holding means 3 to their appropriate positions in order to approximately coincide the tomographic zone P and dental arch T with each other.

Particularly, the drive circuit B is connected to a drive mechanism 7 (in the embodiments, motors are used as shown) having driving means 70 such as a motor (including a linear motor), solenoid, or the like, which allows the drive mechanism 7 to act as a main member for moving the tomograph forming assembly 4 and/or patient holding means 3 to their appropriate positions. In this case, although it is most desirable to operate the drive mechanism 7 automatically by transmitting a command from the drive circuit 5 directly thereto, the drive mechanism 7 can also be operated manually with the use of a manually operable ON/OFF circuit, etc.

The comparing arithmetic circuit 2 implies the difference between the dental arch T and the tomographic zone P upon comparing data of the relative position of the position of the tomographic zone T to the reference point 0 with an electrical signal from the sensor 1 in arithmetic operation and then, determines a direction and amount of the movement of the tomograph forming assembly 4 and/or patient holding means 3. The comparing arithmetic circuit 2 is a combination an A/D converter 21 and microprocessor 22 shown in FIG. 20, an analog type, or a type controlling through phase detection, as the case may be. The comparing arithmetic circuit 2 can execute arithmetic operation upon receiving the position data of the tomographic zone P each time when a command is supplied from a reference distance data producing circuit 6 thereto, further with respect to the position data priorly recorded.

The reference distance data producing circuit 6 supplies the position data of the tomographic zone P to the comparing arithmetic circuit 2 and additionally, acts as a central command circuit in order to send commands for operating the comparing arithmetic circuit 2 and drive circuit 5. Further, it detects structural features (individualities) of the dental arch of patient in configuration, size, etc. Furthermore, according to the detected information, it regulates on a position detected by the sensor 1, transmits to the comparing arithmetic circuit 2 the reference data for comparing arithmetic operation and judgment in the comparing arithmetic circuit 2, and supplies the drive circuit 5 with the reference data of appropriate displacement of the moving mechanism 7 by the drive circuit 5. Particularly, it may contain a circuit which can supply the tomograph forming assembly 4 with data in which adjustment has been made prior so that the configuration of the tomographic zone P provided by the tomograph forming assembly 4 can coincide with a shape of the dental arch T. On the other hand, it will be possible to prior set each component circuit in a state corresponding to the photographing conditions, e.g. in which field a tomograph is taken; dental, otorhinological, or oral surgical field, and whether standard or protruding (projecting frontward) teeth in a dental arch a patient has, in accordance with the information supplied prior to positioning operation from the reference distance data producing circuit 6 to which reference data (for instance, coefficients in forward and backward positioning of the patient holding means 3 and tomograph forming assembly 4) has been supplied. Various functions of the reference distance data producing circuit 6 provide means that in practice, the reference position of the tomographic zone P can be adjusted, under specified conditions, to an area where the dental arch T of patient extends in an approximately overlapping relationship and/or a forwardly or backwardly deviated relationship. The reference distance data producing circuit 6 may be of analog type in which switching is made with a tap on a rehostat, digital type in which data recorded in a memory is selectively read, or the like.

Figure 15:
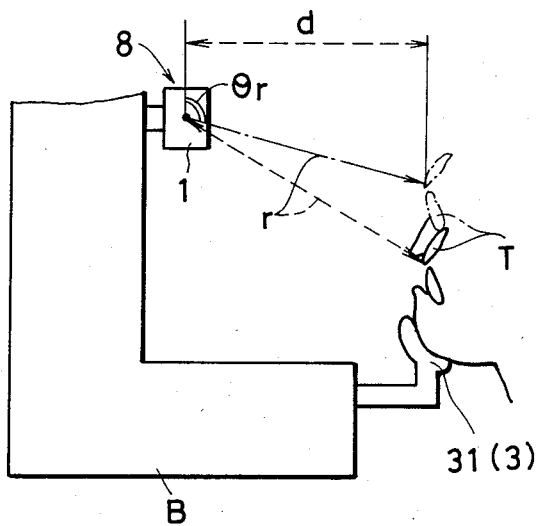
Figure 16:
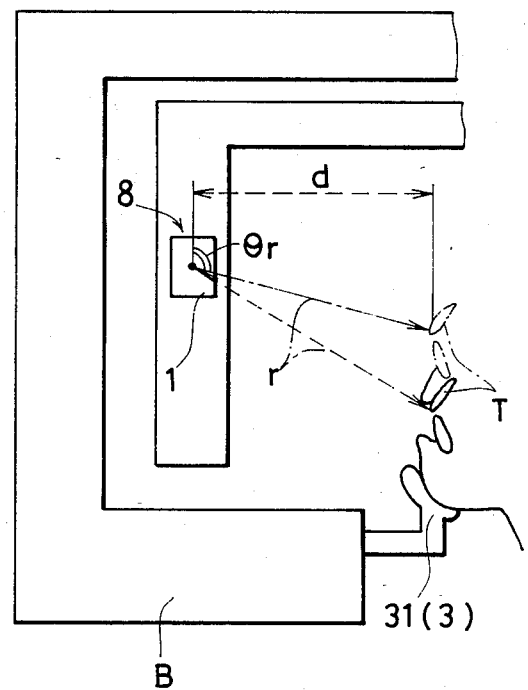

The sensing position changing means 8 is adapted to actuate the sensor 1 to detect precisely regardless of the individualities (e.g. between adult and child, or persons having large and small dental jaws) of the head of patient located on the patient holding means 3. More specifically, the sensing position changing means 8 generally employs a device for adjusting the sensor 1 for vertical positioning (as shown in FIGS. 11 to 14) or for angular setting (as shown in FIGS. 15 and 16). However, it may be a sort of device defined within the principle of the changing means 8, in which pairs of illuminant and receptor components are longitudinally arranged so that one of the pairs (which corresponds to the object to be detected) can be selected by means of manipulation with a dial switch.

The general functions of the above-mentioned devices will be described in conjunction with the drawings. As shown in FIGS. 1 to 10 and FIGS. 20 to 23, the relative position of the dental arch T to the reference point 0 in the X-ray photographing apparatus A is read with the sensor 1 when the head of patient has been placed on the patient holding means 8 and becomes an electrical signal in converting operation. This electrical signal is then supplied, in the embodiments shown, to the comparing arithmetic circuit 2 in which a deviation of the relative position from the relative position of the tomographic zone P to the reference position 0 is calculated and thus, the direction and amount of displacement of the tomograph forming assembly 4 and/or patient holding means 8 will be determined through judgment. The information about the direction and amount of displacement determined by the comparing arithmetic circuit 2 is transferred in the form of an electrical signal to the drive circuit 5 thus to actuate the moving mechanism 7 directly in an automatic mode and through operation of the manually operable ON/OFF circuit in a manual mode. Consequently, the tomograph forming assembly 4 and/or patient holding means 8 moves according to the appropriate direction and amount of displacement determined so that the dental arch T can coincide with the tomographic zone P in a real relationship as shown in FIGS. 2, 4, 6, and 8. When the reference distance data producing circuit 6 is provided, it is artifically turned on prior to the aforesaid movement thus to send an operation command to the sensor 1, comparing arithmetic circuit 2, or drive circuit 5 or to supply the reference data to the same, which provides the fast and accurate positioning.

Each embodiment of the present invention, in the form of a device described above, will be described in more detail in conjunction with the drawings.

Figure 2:
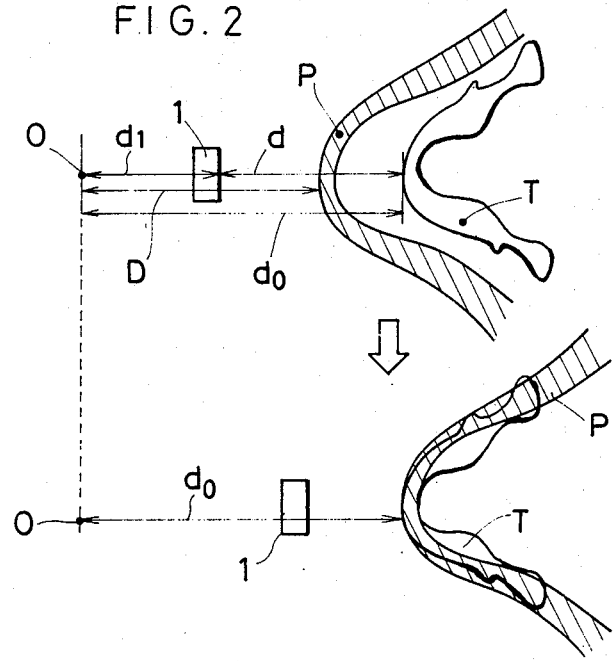
FIG. 2 is an explanatory view of an adjusting mechanism in the embodiment.

FIGS. 1 and 2 illustrate one embodiment in which the tomograph forming assembly 4 is suspendedly mounted for forward and backward movement along the center line of a patient to the main body B by the moving mechanism 7. The sensor 1 is disposed in integral relationship with the tomograph forming assembly 4 on the center line of the main body B and across the rotating circle of the tomograph forming assembly 4. The patient holding means 3 is fixedly mounted to the main body B and a distance d between the sensor 1 and the front teeth of the dental arch T of patient located on the holding means 3 will be detected by the sensor 1. The distance d plus a predetermined distance d1 between the sensor 1 and the reference position 0 is equal to data d0 of the relative position of the dental arch T to the reference point 0 which is thus supplied to the comparing arithmetic circuit 2. Accordingly, the comparing arithmetic circuit 2 compares data D of the relative position of the tomographic zone P to the reference point 0 with the input data d0 from the sensor 1 in arithmetic operation, as set forth above. According to the information produced in this arithmetic operation, the tomograph forming assembly 4 moves by a deviated distance (D-d0) so that the tomographic zone P can approximately coincide with the dental arch T as is shown in FIG. 2. In this embodiment, the forward and backward movement of the tomograph forming assembly 4 activated by the drive circuit 5 is by means of the moving mechanism 7. The moving mechanism 7 includes a drive means 70 comprising a motor 701 and a rack and pinion 702 and mounted in an upper portion of the main body B. Additionally, the moving mechanism 7 has a potentiometer 78 therein, by which the aforesaid movement is detected, so as to allow the tomograph forming assembly 4 to be moved a close distance for positioning adjustment.

Figure 3:
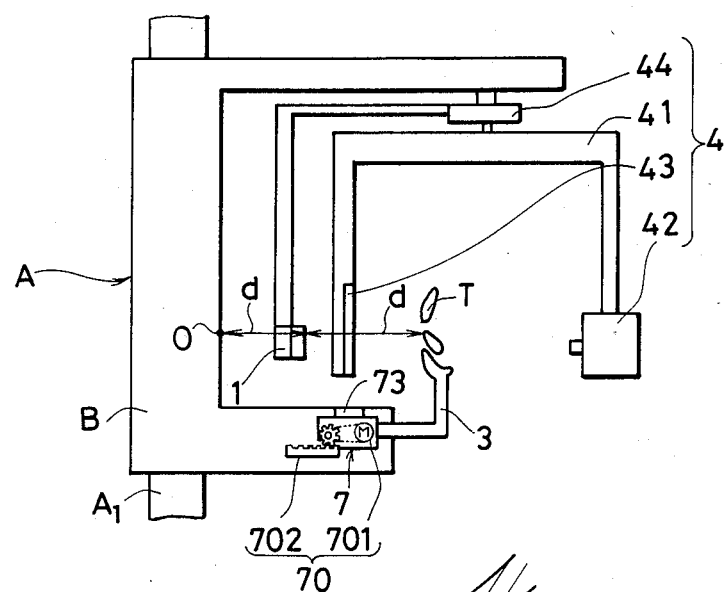
FIGS. 3, 5, and 7 are views similar to FIG. 1, illustrating other embodiments.
Figure 4:
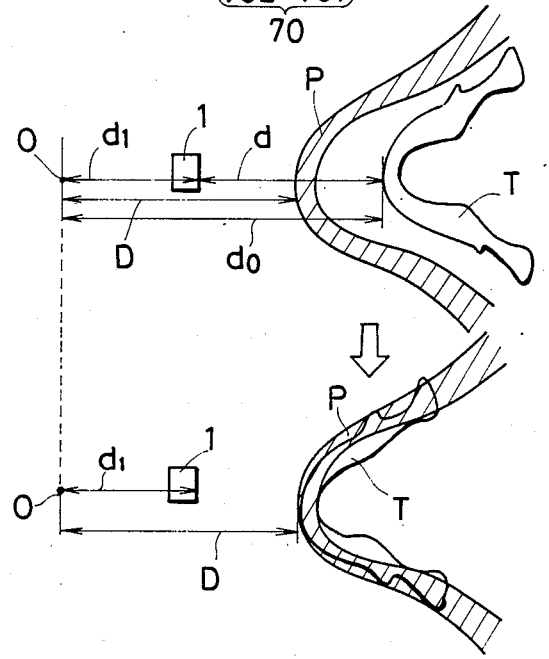
FIGS. 4, 6, and 8 are views similar to FIG. 2, corresponding to such embodiments.

FIGS. 3 and 4 illustrate another embodiment in which the tomograph forming assembly 4 is fixedly mounted to the main body B while the patient holding means 3 is mounted for forward and backward movement along the center line thereof to the main body B by the moving mechanism 7. The sensor 1 is disposed in integral relationship with the tomograph forming assembly 4 in a manner equal to the above described and similarly, the comparing arithmetic circuit 2 compares data d0 of the relative position of the dental arch T from the sensor 1 with the priorly supplied relative position data D of the tomographic zone P in arithmetic operation. Accordingly, the moving mechanism 7 moves the patient holding means 3 upon receiving such information so that the dental arch T can coincide with the tomographic zone P as shown in FIG. 4. The moving mechanism 7 in this embodiment also has a potentiometer 73 so that the patient holding means 3 can move further for precise positioning upon being informed of the result of movement.

Figure 5:
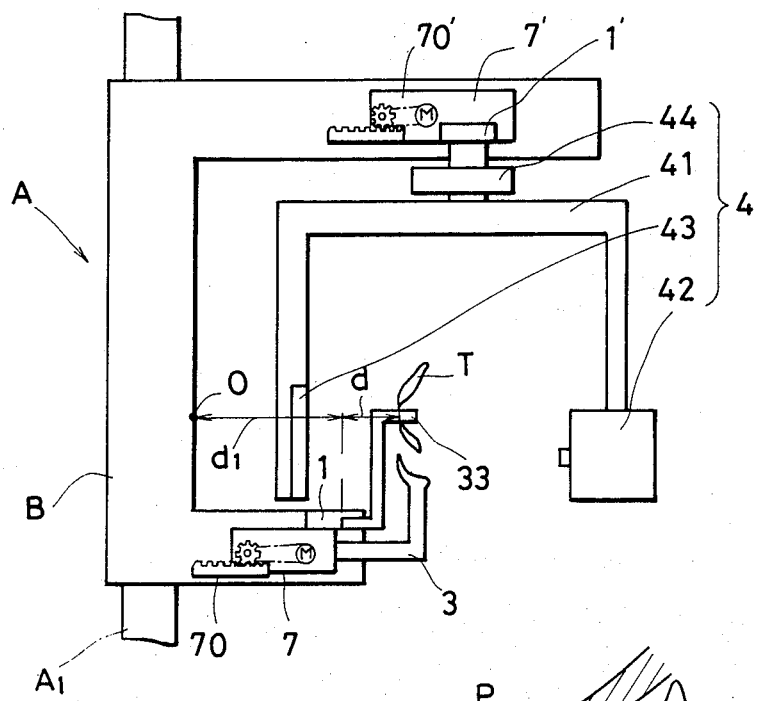
Figure 6:
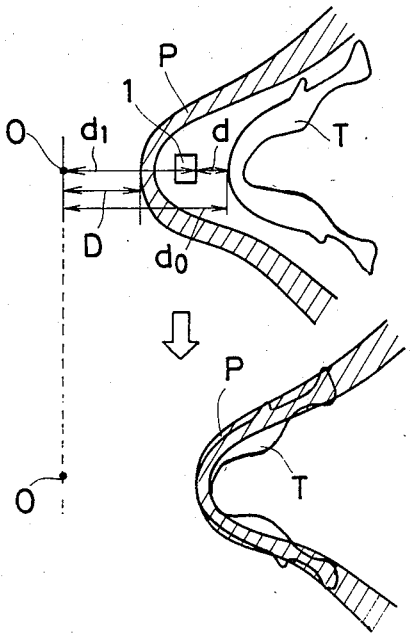

FIGS. 5 and 6 illustrate a further embodiment in which the tomograph forming assembly 4 is suspendedly mounted for forward and backward movement to the main body B by a moving mechanism 7' including a drive means 70', while the patient holding means 3 is mounted for forward and backward movement to the main body B by the moving mechanism 7. The patient holding means 3 has an edge-to-edge occlusion member 33 therein which is connected to the sensor 1 in the form of e.g. a potentiometer, a differential transformer, or a digital linear scale. When the front teeth of the dental arch T of patient are engaging with the edge-to-edge occlusion member 33, a pressure of bit is transferred to the sensor 1 which in reverse detects the position of the front teeth as practically acting as a touch sensor. This position data detected is then output as data d0 of the relative position of the dental arch T to the reference point 0 in the X-ray photographing apparatus A. Additionally, the moving mechanism 7' in the tomograph forming assembly 4 has a position detecting means for the tomograph forming assembly 1' (such as a potentiometer or a differential transformer). Both of the relative position data D of the tomographic zone P from the position detecting means 1' and the relative position data d0 of the dental arch T are supplied to the comparing arithmetic circuit 2 and then, arithmetically compared with each other in the same. As the result, this causes one or both of the moving mechanisms 7 and 7' to actuate so that the dental arch T can approximately coincide with the tomographic zone P in a real relationship as shown in FIG. 6. FIG. 6 shows the result of movement of both the moving mechanisms 7 and 7'. The position detecting means 1' for tomograph forming assembly may also be adapted to check whether the movement of patient holding means 3, if separately executed, is correctly effected for positioning. In this case, the tomograph forming assembly 4 moves for positioning adjustment according to the result of this check.

Figure 7:
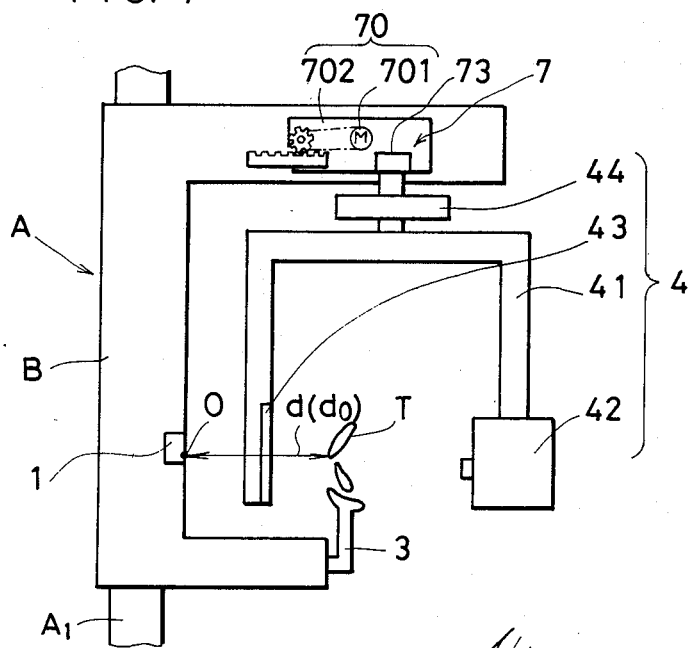
Figure 8:
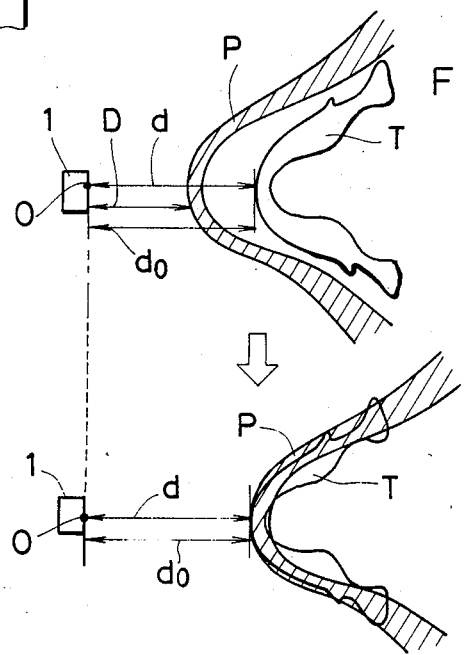

FIGS. 7 and 8 illustrate a further embodiment in which the tomograph forming assembly 4 is suspendedly mounted for forward and backward movement to the main body B by the moving mechanism 7 in an equal manner as shown in FIGS. 1 and 2, while the patient holding means 3 is fixedly mounted to the main body B. The sensor 1 is mounted on the vertical portion of the main body B across the medial line of a patient so as to coincide with the reference point 0. In such an arrangement with the sensor 1 on the main body B, a distance between the tomograph forming assembly 4 and the vertical portion of the main body B is minimized and thus, the whole apparatus can be arranged in a compact form. A distance d from the front teeth of the dental arch T detected by the sensor 1 in this embodiment coincides with the relative position data d0 which is then arithmetically compared with the relative position data D of the tomographic zone P in the comparing arithmetic circuit 2. According to such arithmetically provided data, the moving mechanism 7 actuates the patient holding means 3 to move in an appropriate direction to an appropriate location for positioning. Consequently, the dental arch T can approximately coincide with the tomographic zone P in a real relationship as shown in FIG. 8. The other arrangements in this embodiment are equal to that shown in FIGS. 1 and 2.

Figure 9:
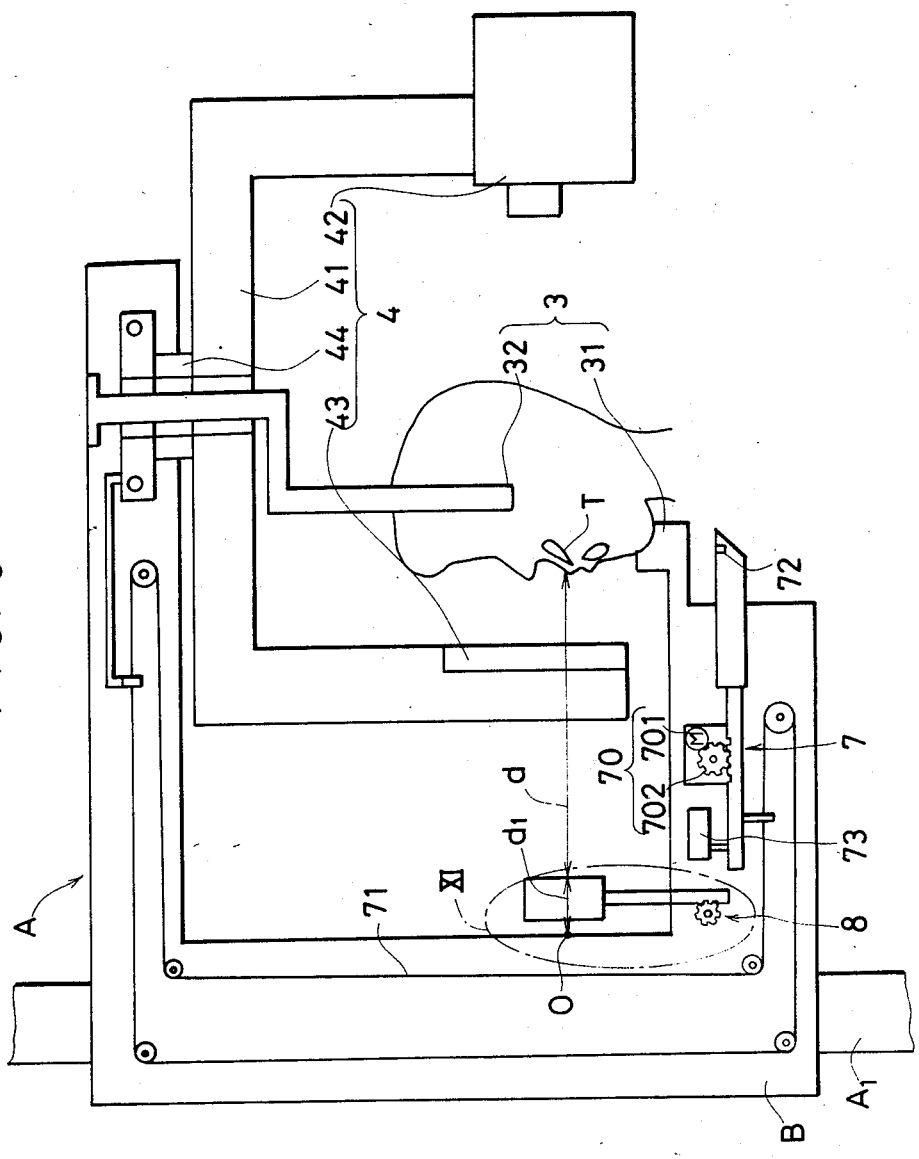
FIG. 9 is an outline side view of a device provided with a sensing position changing means.
Figure 10:
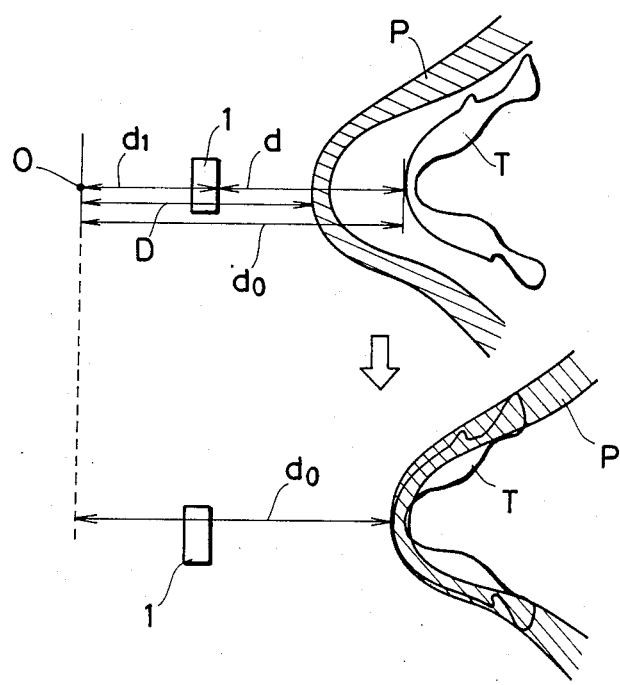
FIG. 10 is an explanatory view of an adjusting mechanism in the embodiment of FIG. 9.
Figure 11:
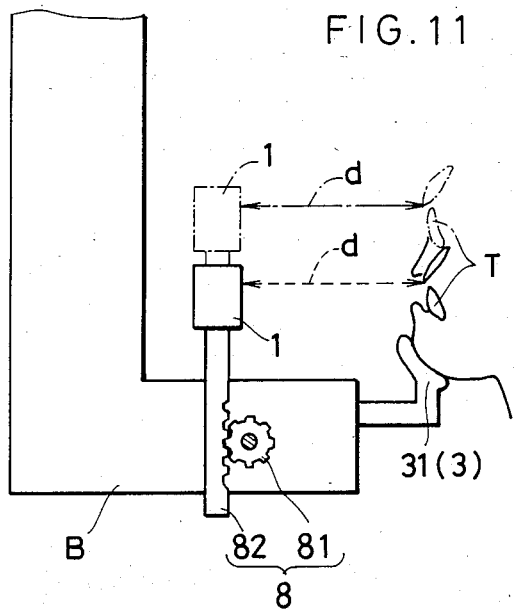
FIG. 11 is an enlarged view of the XI portion of FIG. 9.
Figure 20:
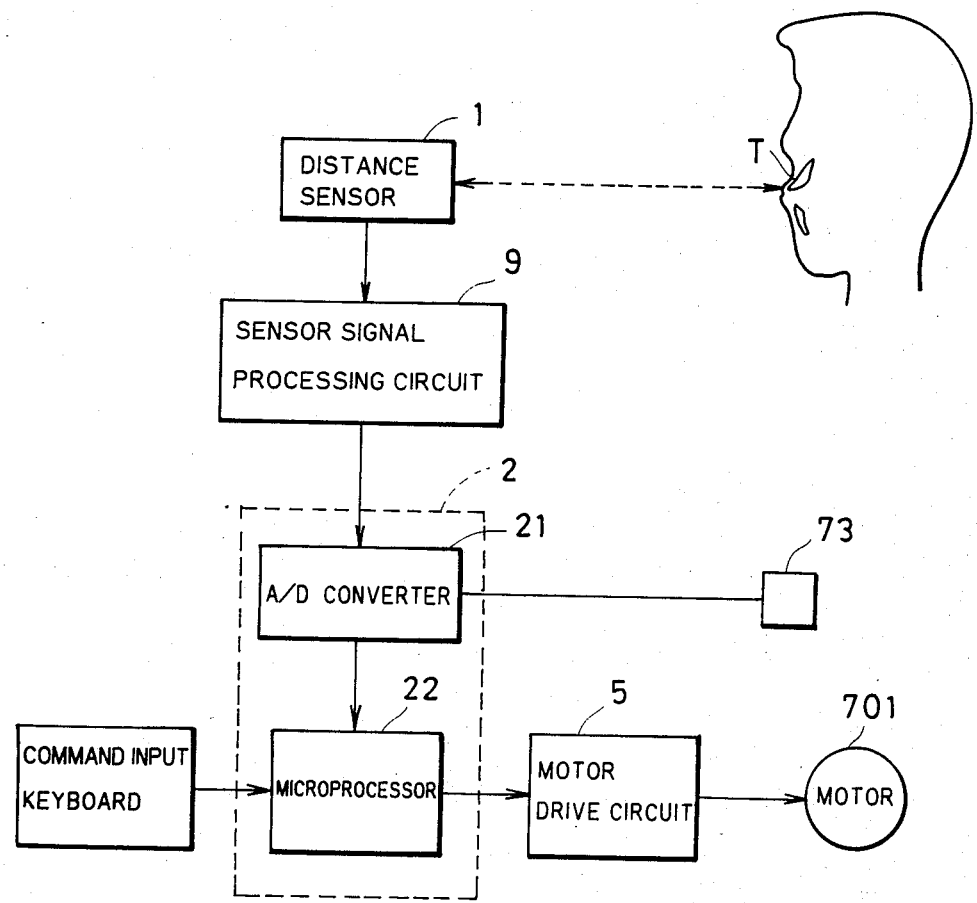
FIG. 20 is a block diagram showing one embodiment of a circuit arrangement according to the present invention.
Figure 21:
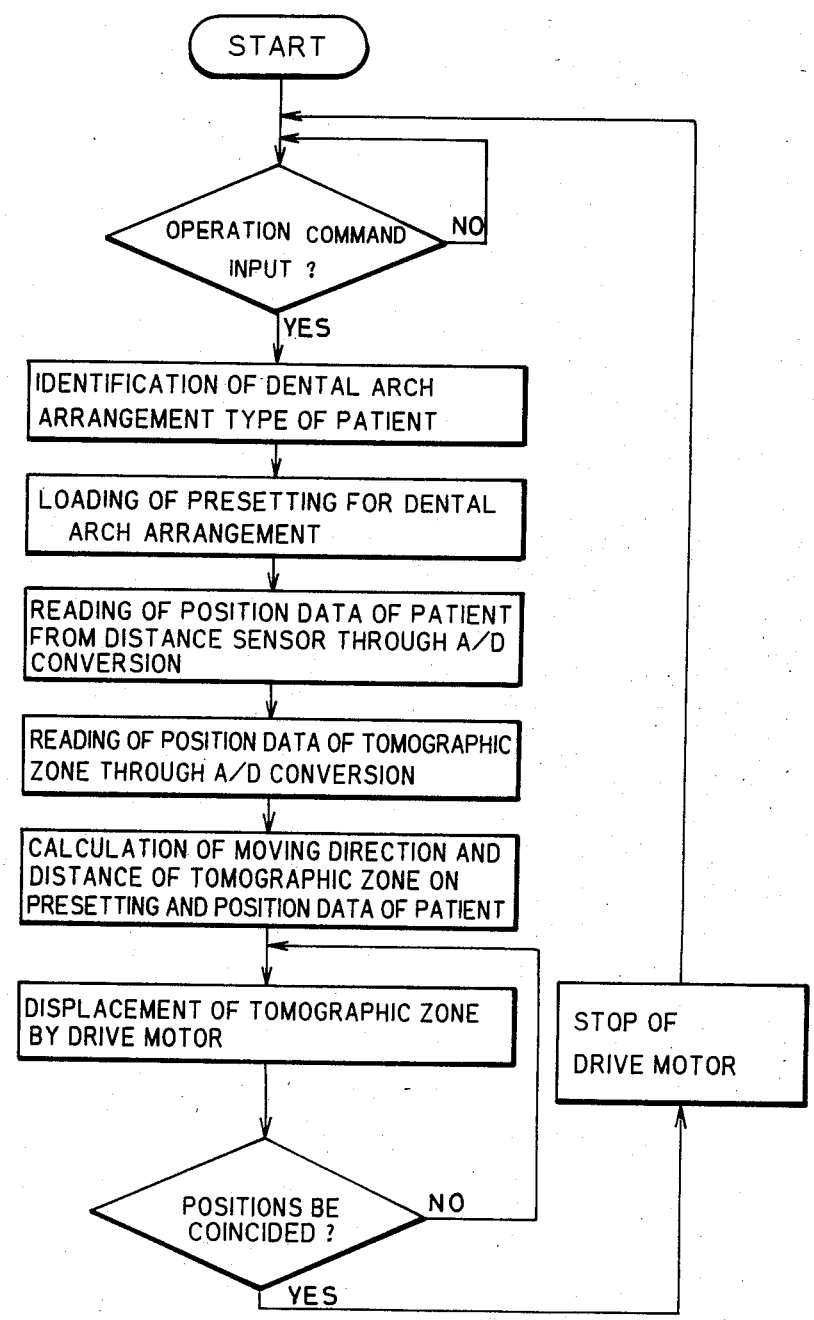
FIG. 21 is a flow chart of the same.

FIGS. 9 to 11 illustrate a still further embodiment in which the vertical positioning of sensor 1 can be made adjustably with the sensing position changing means 8. More particularly, the sensing position changing means 8 is adapted to adjust the sensor 1 for vertical positioning so that a beam of light from the illuminant 11 (described hereinafter) in the sensor 1 can be applied horizontally to the front teeth of the dental arch T. Specifically, the sensing position changing means 8 comprises a pinion gear 81 mounted within a lower portion of the main body B and a rack gear 82 mounted in mesh engagement with the pinion gear 81 for upward and downward movement with the pinion gear 81 rotated by means of manipulation of a manipulating knob (not shown). The sensor 1 is fixedly mounted to the top of the rack gear 82 and thus, can be operated for vertical positioning by the operator using the manipulating knob in order to direct the beam of light from the illuminant 11 horizontally to the front teeth of patient. The patient holding means 3 in this embodiment comprises a chin rest 31 for supporting of the chin of patient and a restricting member 32 hanging from the upper portion of the main body B for restricting the movement of patient such as directional displacement by holding his ear portions, as shown in FIG. 11. Additionally, the patient holding means 3 is disposed in fixed relationship to the main body B, whereby during positioning detection with the sensor 1, the tomograph forming assembly 4 can be moved forward and backward with the patient head being securely placed in the patient holding means 3. In this embodiment, the tomograph forming assembly 4 moves forward and backward upon being activated by the drive circuit 5. The forward and backward movement is by means of the moving mechanism 7 which comprises, a drive means 70 including a motor 701 mounted within a lower portion of the main body B and a rack and pinion 702, and a wire 71 connecting the drive means 70 to the tomograph forming assembly 4. Additionally, there are a beam projector 72 for tomograph designation fixedly mounted to the drive means 70 and a potentiometer 73 for detecting tomographic position mounted to the same in cooperable arrangement. When a movement signal is produced, the motor 701 in the drive means 70 starts rotating to actuate the rack and pinion 702. This motion actuates the tomographic designation beam projector 72 and tomograph forming assembly 4 to move forward and backward simultaneously through movement of the wire 71. The wire 71 is urgingly fitted so that a light beam from the tomographic designation beam projector 72 can be applied constantly across the reference point 0 of the tomographic zone P defined in the tomograph forming assembly 4. This allows the operator to find an approximate position of the tomographic zone P by visually observing a spot of projection on the face of the patient. The potentiometer 73 is adapted to monitor the position of the tomographic zone P constantly, whereby a drive signal is supplied to the drive circuit 5 (as shown in FIG. 20) after the information from the potentiometer 73 is processed in A/D conversion upon entering the A/D converter 21 in the comparing arithmetic circuit 2 and in turn compared in arithmetic operation by the microprocessor 22. Although the tomograph forming assembly 4 is joined with the tomographic indication beam projector 72 by the wire 71 so as to move together with the same in the embodiment, modifications may be possible in which they are driven respectively by separate motors synchronized or not synchronized in electrical operation. On the other hand, the tomographic designation beam projector 72 is provided only for the purpose of assistance to the operator and thus, may be omitted in view of automatic positioning.

For positioning of the patient in the aforesaid embodiment, the head of patient is placed in position on the patient holding means 3 in the first and the sensor 1 is then moved for vertical adjustment by means of the sensing position changing means 8. Then, a distance d between the sensor 1 and the front teeth of the dental arch T of patient is detected in the manner described above and then added to predetermined distance d1 between the sensor 1 and the reference point 0. This information is supplied to the comparing arithmetic circuit 2 as data d0 of the relative position of the dental arch T to the reference point 0 and compared with predetermined data D of the relative position of the tomographic zone P to the reference point 0 in arithmetic operation in the circuit 2. According to the resulting information from the comparing arithmetic circuit 2, the tomograph forming assembly 4 moves a deviated distance (D−d0) so that the tomographic zone P can approximately coincide with the dental arch T.

Additionally, the position of the tomograph forming assembly 4 can be detected by the potentiometer 73 for adjustment of precise positioning thereof in the manner set forth above, if necessary.

FIGS. 12 to 16 show further modifications of the sensing position changing means 8. As shown in FIGS.

Figure 12:
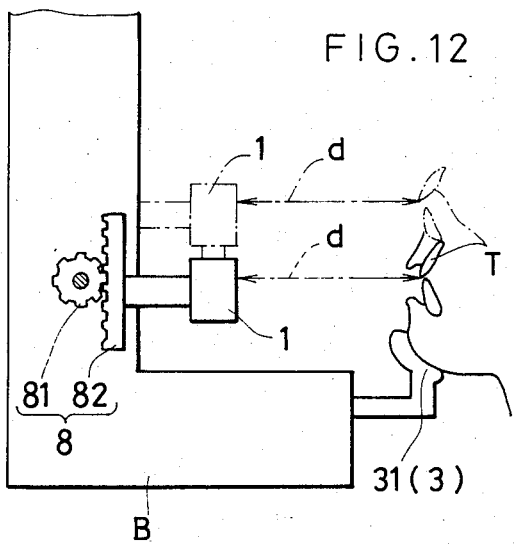
FIGS. 12 to 16 are enlarged views, similar to FIG. 11, of the other embodiments.
Figure 13:
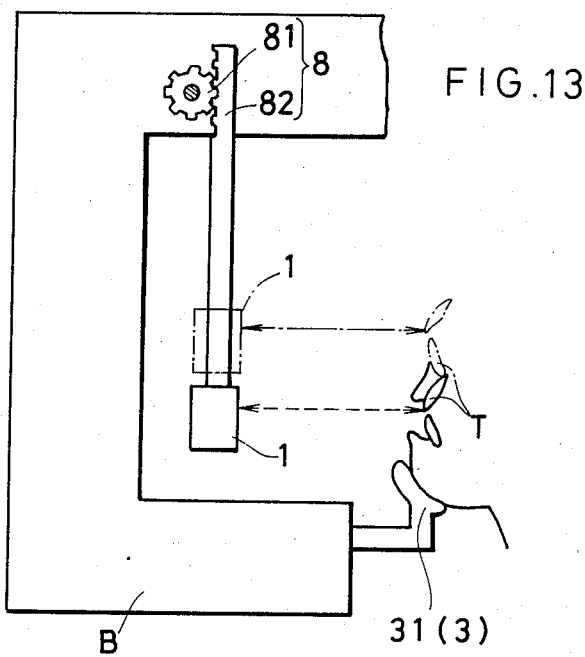

12 and 13, the pinion gear 81 and the rack gear 82 meshing with the pinion gear 81 for vertical movement shown in FIG. 11 are disposed in different regions of the main body B, specifically, in a vertical portion of the body B in FIG. 12 or in an upper portion of the body B in FIG. 13, only to adjust the sensor 1 for vertical positioning with the use of a manipulating knob not shown.

Figure 14:
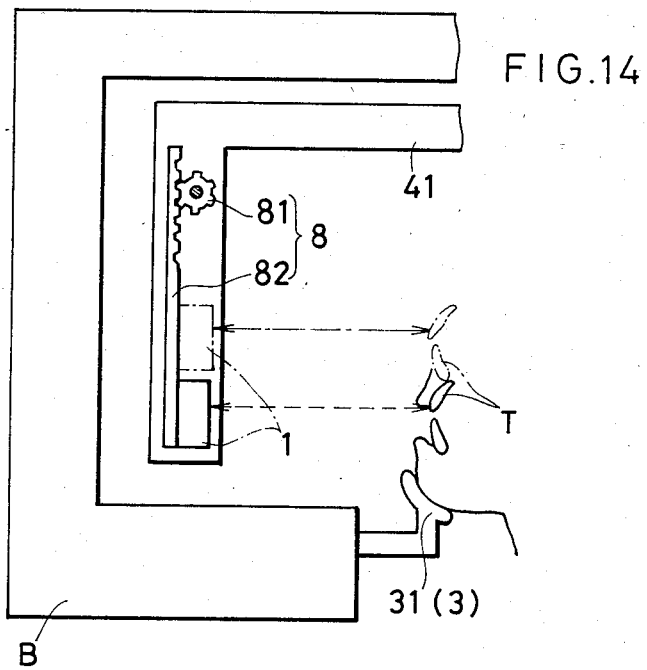

FIG. 14 illustrates the pinion gear 81 and the rack gear 82 meshing with the pinion gear 81 for vertical movement shown in FIG. 11, arranged for vertical adjustment of the sensor 1 mounted to the X-ray film cassette 43 in the tomograph forming assembly 4.

In the embodiments shown in FIGS. 12 to 14, a sensor 1 (FIGS. 18 and 19) is used as will be described later. Similarly, the sensor 1 moves itself for vertical adjustment by means of the sensing position changing means 8 so that a beam of light projected from the illuminant 11 can be applied horizontally to the front teeth of the dental arch T.

FIGS. 15 and 16 show a sensor 1 arranged for angular adjustment by means of the sensing position changing means 8. Particularly, the sensor 1 is pivotably mounted for vertically pivotal movement to the main body B in FIG. 15 or to the rotating arm 41 in FIG. 16. The projecting angle can be adjusted with a manipulating knob not shown, which allows a beam projecting at the angle to be applied to the front teeth of the dental arch T by the operator. A distance r detected by the sensor 1 is inputted together with a projecting angle $\theta r$ to the comparing arithmetic circuit 2 in which a horizontal distance d is calculated. According to the resulting data, a drive signal is then transmitted to the drive circuit 5 via the comparing arithmetic circuit 2.

In the embodiments, the sensor 1 is moved for vertical and angular adjustment with the use of the sensing position changing means 8. Then, the horizontal distance d between the sensor 1 and the objective portion (front teeth in the embodiments) of the dental arch T is measured and according to the measured result, the moving mechanism 7 is actuated so that the tomographic zone P can coincide with the dental arch T. Although the embodiments described are preferred, it is understood that other appropriate means can be employed without limitation to the embodiments.

A sensor 1 used in the preferred form according to the present invention will be described. The sensor 1 comprises an illuminant element 11 and a photoconductive sensing detector element 12 (referred hereinafter to as a PSD element) so as to measure the distance d with the PSD element 12 receiving a ray reflected from the front teeth of the patient dental arch T to which a beam of light from the illuminant 11 is projected.

Figure 18:
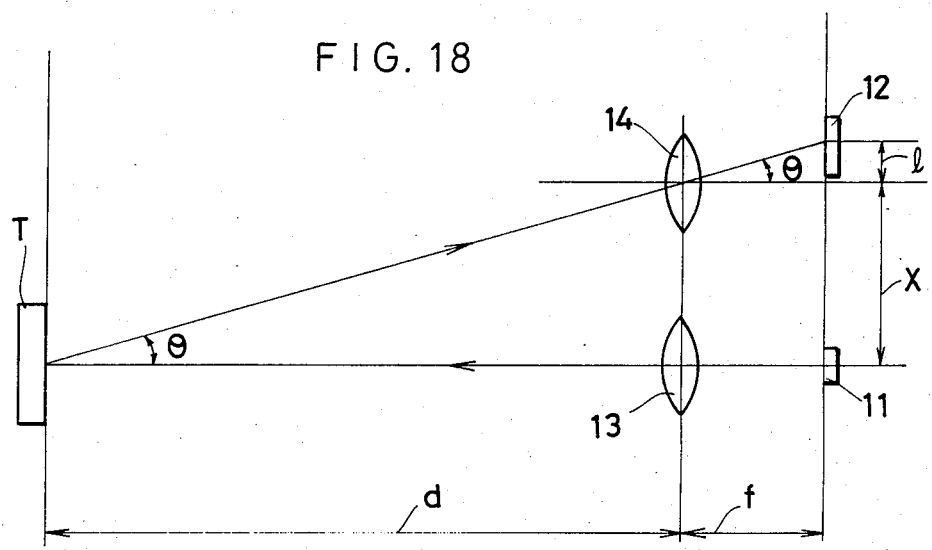

The principles of calculation for measuring the distance d will be described. As shown in FIG. 18, beams of light from the illuminant 11 are concentrated through a projecting lens 13 into an intense beam which is in turn applied to the objective front teeth T (of dental arch). Diffused rays of light reflected from the surfaces of the front teeth T are then focused on the surface of the PSD element 12 with a receiving lens 14. If a distance between the lens 13 and the front teeth T is d, a focal distance of the lens 14 is f, a distance between the centers of the projecting and receiving lenses 13 and 14 is X, and a distance from the center axis of the receiving lens 14 to the focal point on the light receiving surface of the PSD element 12 is l, $$d = \frac{X}{\tan \theta} \qquad 1$$

$$\tan \theta = \frac{l}{f}$$

hence, $$d = \frac{X \cdot f}{l} \qquad 2$$

When the value of l is measured as the values of X and f are known, the distance d will be obtained.

Figure 19:
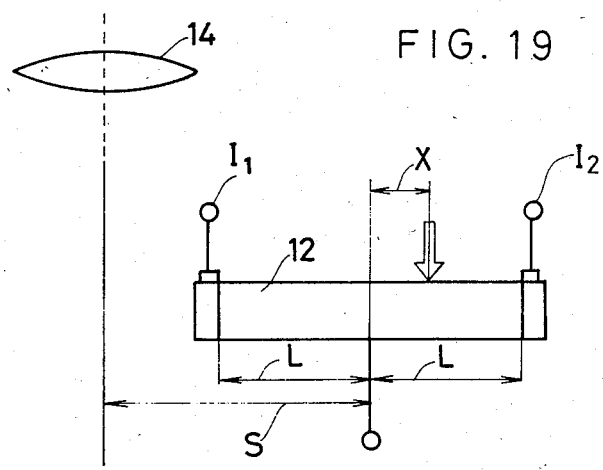
FIG. 19 is an explanatory view of sensors disposed in distinct arrangement.

Next, the distance d will be calculated in accordance with the principles of the PSD element 12. As shown in FIG. 19, $$\frac{x}{L} = \frac{I2 - I1}{I1 + I2}, x = L \frac{I2 - I1}{I1 + I2}$$

(where x=distance from the center of PSD element 12 to a light receiving point, L=distance from the center of PSD element 12 to an electrode, and I1, I2=photoelectric current at the ends of PSD element 12). When L is constant, $(I2-I1)/(I1+I2)$ is proportional to the distance x. On the other hand, when $$l = x + s$$

(where s=distance between the center axis of receiving lens 14 and PSD element 12), and $$x = L \frac{I2 - I1}{I1 + I2},$$

the equation 2 is $$d = \frac{x \cdot f}{L (I2 - I1) / (I1 + I2) + s}$$

If $(I2 - I1) / (I1 + I2) = \delta$, $$d = \frac{x \cdot f}{L \cdot \delta + s}$$

Then, d is a function of $\sigma$ or $(I2-I1)/(I1+I2)$. Accordingly, when $\sigma$ is output as a direct current, d will be obtained.

Figure 17:
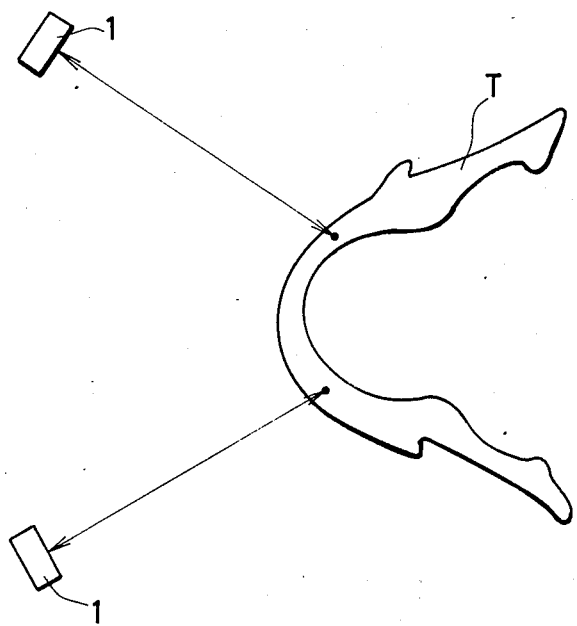
FIGS. 17 and 18 illustrate the principles of sensors employed according to the present invention.

FIG. 17 illustrates another arrangement for the sensor 1 in which two of the sensors 1, 1 are disposed to face the left and right canine teeth of dental arch T and will provide detecting position data respectively for the positioning set forth above. In this embodiment, the two-dimensional position data are given by the two sensors 1, 1. This makes it possible to provide improved accuracy in positioning through arithmetic comparing operation on the individual physical features of a patient with the predetermined model setting in the comparing arithmetic circuit 2. As the result, the accuracy in positioning will be improved when the plurality of sensors 1 are used for increasing detecting points on the dental arch T.

Figure 22:
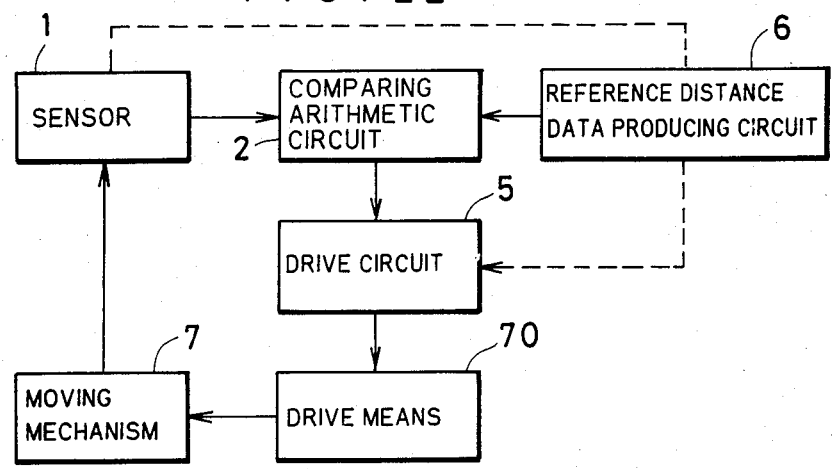
FIGS. 22 and 23 are block diagrams showing other embodiments of the circuit arrangement.
Figure 23:
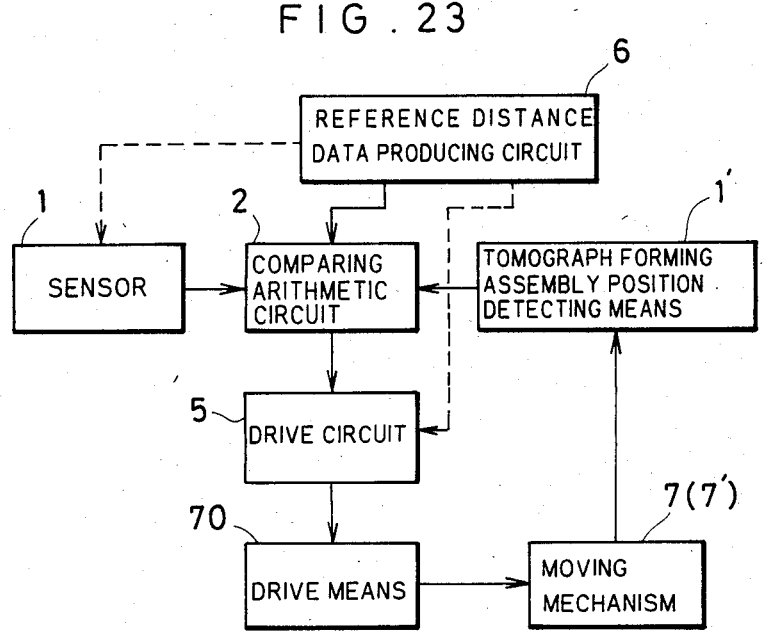

FIGS. 20, 22, and 23 are block diagrams showing various arrangements of the circuits used in a device of the present invention.

FIG. 20 is a block diagram of a circuit arrangement preferably utilized in all the embodiments described above. The detecting position data of the dental arch T from the sensor 1 are arithmetically compared with the position data of the tomographic zone P in the comparing arithmetic circuit 2. The arithmetic circuit 2 includes an A/D converter 21 for processing the detection data from the sensor 1 in A/D conversion and a microprocessor 22 for sending a signal to the drive circuit 5 upon comparing the the operated data from the A/D converter 21 with the presupplied position data of the tomographic zone P. A sensor signal processing circuit 9 is interposed between the sensor 1 and the comparing arithmetic circuit 5. A position detecting signal from the sensor 1 is converted into a digital signal in the A/D converter 21 after being processed in the signal processing circuit 9 and then, transmitted to the microprocessor 22. The operator can select one appropriate model information from the multiplicity of model information recorded in the microprocessor 22 with the use of a keyboard upon recognizing the physical features of the patient such as dentition, shape and size of teeth arrangement, etc. The processed data from the processing circuit 9 then is arithmetically processed in relation to the tomographic zone P corresponding to the selected model information by the microprocessor 22 which in turn sends a signal for motion to the drive circuit 5.

FIG. 22 is a block diagram adapted to the embodiments shown in FIGS. 1 to 4. In the embodiments, while various conditions are determined by the reference distance producing circuit 6, the information of detected position from the sensor 1 is supplied to the comparing arithmetic circuit 2 to which the relative position data of the tomographic zone P has been supplied. Then, in the comparing arithmetic circuit 2, a deviation in the relative position of the tomographic zone P to the dental arch T is calculated and also, the direction and amount of movement of the tomographic zone P or dental arch T are determined. Accordingly, the drive circuit 5 operates according to the data from the comparing arithmetic circuit 2 thus to activate the moving mechanism 7. The resulting action by the moving mechanism 7 is detected once more by the sensor 1, which permits the movement to be adjusted.

FIG. 23 is a block diagram adapted to the embodiments shown in FIGS. 5 to 8. In the embodiments, the detection information from the sensor 1 and position detecting means 1' for tomograph forming assembly is supplied to the comparing arithmetic circuit 2 in which the detection information is compared with the presupplied relative position data of the tomographic zone P. Then, according to the result from arithmetic comparing operation, the dental arch T or tomographic zone P moves forward and backward in the manner described above. The result from movement by the moving mechanism 7 is sent in feedback to the tomograph forming assembly position detecting means 1' for readjustment of the movement of the tomographic zone P.

As set forth above, a relative position of the dental arch of patient is detected by the sensor 1 and compared with the relative position data of the tomographic zone in arithmetic operation so that the tomographic zone or dental arch can be displaced for coincidence according to the resulting information, which thus permits a beginner to achieve positioning precisely and readily. In this way, it is possible to provide improved quality of an X-ray picture, sharply reduce failures in X-ray photographing resulting from mispositioning and thus, minimize rephotographing or unnecessary exposure of the patient to X-ray. When the comparing arithmetic circuit is provided in a system, the operation of positioning will be facilitated and the accuracy in positioning will further be improved. Additionally, when the sensor is adjusted for vertical and angular setting with the sensing position changing means, the relative position of the dental arch of patient can precisely be detected regardless of the individualities of the head of patient.

Although the embodiments described above employ a method for detecting a relative position of the dental arch directly with the sensor, it will be possible to detect a distinct portion other than the head of a patient and find the relative position of the dental arch through arithmetic operation on the detected data.

Furthermore, although the device according to the present invention is described for use with a dental jaw panorama X-ray photographing apparatus in which the object to be photographed is a dental arch, it can be utilized with equal success in a panorama X-ray photographing apparatus for distinct medical fields in which the object to be tomographed is other than the dental arch, for example, otolaryngology in which the objects to be required are a dental arch in otorhinol areas, maxillary articulations (both left and right sides or one side), and areas of maxillary hollow, or oral surgery in which a face portion is the object in addition to a dental portion.

We claim:

1. A medical panorama X-ray photographing apparatus, comprising a position detecting sensor for detecting the relative position of a dental arch to be examined to the X-ray photographing apparatus, a comparing arithmetic circuit for comparing detected position data from the sensor with data of the relative position of a tomographic zone to the X-ray photographing apparatus, and a drive circuit for relatively displacing a tomograph forming assembly and a patient holding means by means of an output from said comparing arithmetic circuit so that the subject and tomographic zone can coincide with each other, and said sensor is a non-contact or contact type sensor arranged so as to be confronted with at least the front teeth of said dental arch and one of the patient holding means and tomograph forming assembly and a main body in the X-ray photographing apparatus.

2. An apparatus as defined in claim 1, wherein said drive circuit is connected to a moving mechanism including a drive means, such that said moving mechanism actuates the tomograph forming assembly for forward and backward movement upon receiving an output from said comparing arithmetic circuit.

3. An apparatus as defined in claim 1, further comprising, a sensing position changing means for said sensor.

4. An apparatus as defined in claim 3, wherein said sensor is disposed on the main body of the X-ray photographing apparatus or in the tomograph forming assembly.

5. An apparatus as defined in claim 3, wherein said sensing position changing means adjusts said sensor for vertical setting.

6. An apparatus as defined in claim 3, wherein said sensing position changing means adjusts said sensor for angular setting.

7. An apparatus as defined in claim 3, wherein the position data of the subject and tomographic zone are arithmetically compared with each other.

8. An apparatus as defined in claim 3, wherein the comparing is reformed by an arithmetic circuit which comprises an A/D converter for processing detection data from said sensor in A/D conversion and a microprocessor for comparing arithmetic data from said A/D converter with the presupplied position data of the tomographic zone and additionally, supplying a signal to said drive circuit.

9. An apparatus as defined in claim 3, wherein the tomograph forming assembly comprises a horizontal rotating arm, an X-ray generator and X-ray film cassette disposed in an opposite relationship to each other on the ends of the arm respectively, and a rotating drive mechanism for moving the arm in a configuration along the subject.

10. An apparatus as defined in claim 8, wherein said drive circuit is connected to a moving mechanism including drive means, whereby said moving mechanism actuates the tomograph forming assembly for forward or backward movement upon receiving an output from said comparing arithmetic circuit.

11. A medical panorama X-ray photographing apparatus, comprising a position detecting sensor for detecting the relative position of a subject to be examined to the X-ray photographing apparatus, a comparing arithmetic circuit for comparing detected position data from the sensor with data of the relative position of a tomographic zone to the X-ray photographing apparatus, and a drive circuit for relatively displacing a tomograph forming assembly and a patient holding means by means of an output from said comparing arithmetic circuit so that the subject and tomographic zone can coincide with each other, and wherein said position data of said tomographic zone is supplied to said comparing arithmetic circuit by means of a reference distance producing circuit, and said reference distance data producing circuit sets the reference position of the tomography to a position approximately coincided with the position of a dental arch of a patient.

* * * * *

UNITED STATES PATENT AND TRADEMARK OFFICE
CERTIFICATE OF CORRECTION

PATENT NO. : 4,907,251

DATED : March 6, 1990

INVENTOR(S) : Keisuke Mori, et al.

It is certified that error appears in the above-identified patent and that said Letters Patent is hereby corrected as shown below: ON TITLE PAGE: Item [19] "Mark" should be--Mori--.

Column [75] Inventors: Change "Keisuke Mork, Kyoto; Takao Makino Shiga; Kazuo Nishikawa, Kyoto; Yoshiaki Iwato; Takahiro Yoshimura, both of Osaka, all of Japan" to --Keisuke Mori, Kyoto; Takao Makino, Shiga; Kazuo Nishikawa, Kyoto; Yoshiaki Iwato; Takahiro Yoshimura, both of Osaka, all of Japan-- and ADD:

Column [30] Foreign Application Priority Data

Mar. 13, 1987 [JP] Japan ..... 62-058524
Jun. 11, 1987 [JP] Japan ..... 62-089890

Signed and Sealed this

Twenty-third Day of April, 1991

*Attest:*

HARRY F. MANBECK, JR.

*Attesting Officer*      *Commissioner of Patents and Trademarks*